United States Patent [19]

Takano et al.

[11] 4,317,918
[45] Mar. 2, 1982

[54] PROCESS FOR PREPARING ALCOHOLS

[75] Inventors: Tetsuo Takano; Gohu Suzukamo; Masaru Ishino, all of Osaka; Kiyoshi Ikimi, Kyoto, all of Japan

[73] Assignee: Sumitomo Chemical Co., Ltd., Osaka, Japan

[21] Appl. No.: 203,486

[22] Filed: Nov. 3, 1980

[30] Foreign Application Priority Data

Nov. 5, 1979 [JP] Japan .............................. 54/143549
Nov. 21, 1979 [JP] Japan .............................. 54/151762
Nov. 26, 1979 [JP] Japan .............................. 54/153225

[51] Int. Cl.$^3$ .................. C07C 29/136; C07C 31/02; C07C 33/34; C07C 33/46; C07C 51/10
[52] U.S. Cl. .................................... 562/406; 568/807; 568/808; 568/812; 568/814; 568/861; 568/885; 568/888; 568/831
[58] Field of Search ................ 562/406; 568/807, 808, 568/812, 814, 885, 861, 831

[56] References Cited

U.S. PATENT DOCUMENTS 3,579,552  5/1971  Craddock et al. ................. 562/406
3,689,553  9/1972  Schultz .............................. 562/406
3,770,837 11/1973  Faustritsky et al. ............... 568/814

OTHER PUBLICATIONS

*Journal of Organic Chemistry*, vol. 24, pp. 1847–1854, (1959).

*Primary Examiner*—Natalie Trousof
*Assistant Examiner*—Frederick W. Pepper
*Attorney, Agent, or Firm*—Birch, Stewart, Kolasch & Birch

[57] ABSTRACT

An alcohol is produced in a high selectivity with a good yield from the corresponding carboxylic acid by reducing the latter with hydrogen in the presence of a rhenium catalyst in the coexistence of an organic base. An arylacetic acid, which is included in the starting carboxylic acid, can be produced in an excellent yield from the corresponding aryl aldehyde by reacting the latter with carbon monoxide and water in the presence of rhodium or its compound and hydrogen iodide.

12 Claims, No Drawings

PROCESS FOR PREPARING ALCOHOLS

The present invention relates to a process for preparing alcohols. More particularly, it relates to a process for preparing alcohols from the corresponding carboxylic acids in a single step with a high selectivity and an excellent yield.

For production of alcohols from carboxylic acids, there is well known a process wherein the starting carboxylic acids are first esterified, and the resultant esters are reduced with a reducing agent such as a metal hydride or with hydrogen in the presence of a catalyst such as copper chromite. This process, however, requires a large amount of expensive reducing agents or uses a high pressure of hydrogen as well as a high temperature. In addition, the esterification of the starting carboxylic acids prior to the reduction is inevitable. These are disadvantageous from the viewpoint of industrial application.

There is also known a process for preparing alcohols from carboxylic acids in a single step by the use of a reducing agent such as a metal hydride (e.g. lithium aluminum hydride) in an ethereal solvent. However, this process requires a great amount of expensive reducing agents. In addition, it necessitates troublesome operations such as separation of by-products, for instance, aluminum hydroxides.

As a catalytic reduction process for conversion of carboxylic acids into the corresponding alcohols in a single step, there is known the one using a ruthenium catalyst as described in J.Am.Chem.Soc., 77, 3766 (1955), but this process requires a high pressure of hydrogen of more than 500 atm. In another process using a ruthenium catalyst as described in Chem.Ber., 90, 750 (1957), there is recognized a serious drawback; i.e. in case of reducing aromatic carboxylic acids, the undesirable hydrogenation of the aromatic ring may take place predominantly so that only a small amount of the desired aromatic alcohols are sometimes obtainable.

Production of alcohols from carboxylic acids using a rhenium catalyst is reported in J.Org.Chem., 24, 1847 (1959), ibid., 28, 2343, 2345 and 2347 (1963), etc. However, the reaction requires a high pressure of hydrogen and a long period of time, unless $PtO_2$ is added to the reaction system and $Re_2O_7$ is treated with hydrogen beforehand. In addition, many experiments reveal the by-production of esters or methylated compounds in considerable amounts. For instance, in J.Org.Chem., 24, 1847 (1959), it is noted that reduction of phenylacetic acid with hydrogen in the presence of $Re_2O_7$ without any solvent affords a mixture of 2-phenylethanol and 2-phenylethyl phenylacetate. From the experimental data therein, it is seen that 2-phenylethyl phenylacetate is concurrently formed in a great amount. Thus, this process is also unsatisfactory for industrial production of alcohols.

As the result of an extensive study, it has now been found that the coexistence of an organic base in the reaction system for reduction of a carboxylic acid with hydrogen in the presence of a rhenium catalyst shows remarkable enhancement of the reaction rate and the selectivity to the corresponding alcohol and therefore affords such alcohol in an excellent yield.

According to the present invention, there is provided a process for the production of an alcohol from the corresponding carboxylic acid by directly reducing said carboxylic acid with hydrogen in the presence of a rhenium catalyst, characterized in that an organic amine exists in the reaction system so that the alcohol is produced in a high selectivity along with an excellent yield.

The starting carboxylic acid used in the process of this invention may be any organic compound having at least one carboxyl group insofar as any atom or group which prevents or interferes the relevant reduction is not present in the molecule. Such carboxylic acids usually have a molecular weight of up to 500 and include aliphatic, aromatic and araliphatic carboxylic acids which are constituted with a substituted or unsubstituted hydrocarbon skeleton having at least one carboxyl group. In general, the presence of only one carboxyl group is preferred. Thus, typical examples of the starting carboxylic acid are those of the formula: R-COOH wherein R is a substituted or unsubstituted, aliphatic, aromatic or araliphatic hydrocarbon group. As the substituent which may be present on the hydrocarbon group, there may be for example a lower alkyl, lower alkoxy, aryloxy (e.g. phenoxy, naphthoxy), hydroxyl, etc.

Specific examples of the carboxylic acid include aliphatic carboxylic acids (e.g. acetic acid, propionic acid, butyric acid, capronic acid, caprylic acid, capric acid, lauric acid, stearic acid, isobutyric acid, oxalic acid, malonic acid, maleic acid, succinic acid, glutaric acid, adipic acid, glycolic acid, lactic acid, malic acid, oxycaproic acid, monofluoroacetic acid, monochloroacetic acid), aromatic carboxylic acids (e.g. benzoic acid, toluic acid, phthalic acid, naphthoic acid, phenoxybenzoic acid), alicyclic carboxylic acids (e.g. cyclohexanecarboxylic acid), araliphatic carboxylic acids (e.g. phenylacetic acid, 4'-methylphenylacetic acid), etc.

Among various carboxylic acids usable as the starting material, the most preferred are arylacetic acids, which are representable by the formula:

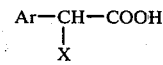

wherein Ar is a substituted or unsubstituted, monocyclic or condensed polycyclic, aromatic hydrocarbon group and X is hydrogen or $C_1$-$C_6$ alkyl. When Ar represents a substituted or unsubstituted monocyclic aromatic hydrocarbon group, it may be preferably a phenyl group bearing optionally one to three substituents chosen from an alkyl having not more than 6 carbon atoms, an alkoxy having not more than 6 carbon atoms, aryl having not more than 20 carbon atoms, an aralkyl having not more than 20 carbon atoms, an aryloxy having not more than 20 carbon atoms and a halogen, said alkyl and alkoxy being optionally substituted with not more than 6 fluorine atoms. When Ar represents a substituted or unsubstituted condensed polycyclic aromatic hydrocarbon group, it may be preferably a naphthyl, anthranyl or phenanthryl group bearing optionally one to three substituents chosen from an alkyl having not more than 6 carbon atoms, an alkoxy having not more than 6 carbon atoms and a halogen. Specific examples of the arylacetic acids are as follows: phenylacetic acid, 2'-methylphenylacetic acid, 3'-methylphenylacetic acid, 4'-methylphenylacetic acid, 2'-ethylphenylacetic acid, 4'-ethylphenylacetic acid, 2'-isopropylphenylacetic acid, 4'-isopropylphenylacetic acid, 4'-t-butylphenylacetic acid, 4'-phenylphenylacetic acid, 4'-benzylphenylacetic acid, 2',4'-dimethylphenylacetic acid, 2'-methyl-4'-ethylphenylacetic acid, 2'- methoxyphenylacetic acid, 4'-methoxyphenylacetic acid, 4'-ethoxyphenylacetic acid, 3'-phenoxyphenylacetic acid, 4'-trifluoromethylphenylacetic acid, 2'-monofluoromethoxyphenylacetic acid, 4'-monofluoromethoxyphenylacetic acid, 4'-fluorophenylacetic acid, 2'-chlorophenylacetic acid, 4'-chlorophenylacetic acid, α-methylphenylacetic acid, 1'-naphthylacetic acid, 2'-naphthylacetic acid, 1'-anthranylacetic acid, 4'-methyl-1'-naphthylacetic acid, α-methyl-1'-naphthylacetic acid, etc. Particularly preferred are 4'-methylphenylacetic acid, 4'-t-butylphenylacetic acid, 2',4'-dimethylphenylacetic acid, etc.

The process of this invention may be carried out without using any reaction medium. In order to smoothly run the reaction however, the use of an appropriate solvent as the reaction medium is preferred. The solvent usable as the reaction medium may be any inert one conventionally employed for reduction such as ethers, aliphatic hydrocarbons, alicyclic hydrocarbons, aromatic hydrocarbons and water. Examples of preferred solvents are dioxane, tetrahydrofuran, diphenyl ether, diglyme, benzene, toluene, xylene, water, etc. These solvents may normally be used in such an amount that the concentration of the starting carboxylic acid is made from 1 to 80% by weight, particularly from 5 to 50% by weight.

As the rhenium catalyst, there may be used rhenium or its compound. The rhenium compound may be any one which can be reduced to give rhenium or oxides of rhenium of a lower oxidation state. Examples of such rhenium compounds are dirhenium heptoxide, rhenium trioxide, rhenium dioxide hydrate, dirhenium trioxide, rhenium monoxide, rhenium pentachloride, perrhenic acid, ammonium perrhenate, dirhenium heptoxide-dioxane complex, dirhenium heptoxide-tetrahydropyrane complex, etc. Other rhenium compounds such as rhenium oxides and their hydrates, oxy acids of rhenium and their salts and complexes in which organic ligands coordinate to rhenium atom are also usable. Among these rhenium compounds, preferred are rhenium oxides, particularly of a lower oxidation state, because their catalytic activity is superior. Such a lower oxidation state can be readily attained by thermal decomposition or partial reduction of higher oxidation state rhenium compounds. Specific examples of favorable rhenium catalysts are rhenium, rhenium monoxide, dirhenium monoxide, dirhenium trioxide, rhenium dioxide, dirhenium pentoxide, etc. They may be used alone or in combination.

The rhenium catalyst may be as such introduced into the reaction system. Alternatively, it may be used fixed on a porous carrier, for example, activated carbon, alumina, celite or zeolite.

If necessary, the rhenium catalyst may be subjected to reduction treatment prior to its use in the process of the invention. In the alternative, such reduction pretreatment may be in situ effected under the hydrogen atmosphere in the reaction system according to this invention. The catalytic effect of the rhenium catalyst is markedly enhanced by the coexistence of an organic base. For instance, in the reduction of an arylacetic acid to a 2-arylethanol, the successive reaction to an ethyl group as well as the side reaction (i.e. esterification) is sufficiently inhibited, and the selectivity to the 2-arylethanol is highly increased.

As the organic base, there may be used any one chosen from a wide scope of organic compounds having a lone pair electron, containing nitrogen atom, phosphorus atom, etc. Typical examples are nitrogen-containing compounds such as amines, imines, pyridine and morpholine, phosphorus compounds such as phosphines, etc. Preferred are aliphatic amines (e.g. triethylamine, tri-n-butylamine) as well as aliphatic nitrogen-containing compounds readily convertible into aliphatic amines by reduction with hydrogen; phosphines (e.g. triphenylphosphine, tri-n-butylphosphine) are also preferred. The amount of the organic base is varied depending on the one being utilized, and may be usually from $10^{-4}$ to 10 mole, preferably from $10^{-2}$ to 1 mole, to one mole of the rhenium catalyst. The organic base may be either added to the rhenium catalyst prior to the reaction or introduced into the reaction system separately and independently from the rhenium catalyst compound.

The reaction in the process of this invention may be normally effected at a temperature of 80° to 250° C., particularly of 100° to 180° C., under a hydrogen partial pressure of 50 to 500 atm, especially of 80 to 200 atm. The reaction time depends upon the reaction temperature and may be usually from 0.1 to 10 hours. The reaction may be carried out batchwise or continuously. In case of the batchwise procedure, the catalyst may be recovered from the reaction mixture by a conventional separation technique such as filtration or precipitation and, if necessary, reactivated and submitted again to the reaction. The catalyst may be used in a fixed bed or in a slurry phase.

As the result of the above reaction, there is produced an alcohol corresponding to the starting carboxylic acid with a high selectivity and in an excellent yield. Separation of the produced alcohol from the reaction mixture may be accomplished by a per se conventional procedure such as distillation and extraction.

As stated above, the produced alcohol corresponds to the carboxylic acid used as the starting material. When the starting carboxylic acid is representable by the formula: R-COOH wherein R is as defined above, the produced alcohol may be represented by the formula: R—CH₂OH wherein R is as defined above. Thus, the arylacetic acid of the formula:

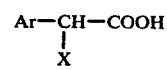

wherein Ar and X are each as defined above affords the corresponding alcohol of the formula:

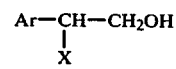

wherein Ar and X are each as defined above.

The alcohols produced by the process of this invention are per se useful as industrial chemicals and also as intermediates in the production of resins, pesticides, pharmaceuticals, etc. For instance, phenethyl alcohol derivatives of the formula:

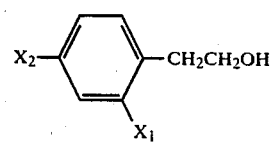

wherein $X_1$ is hydrogen or methyl and $X_2$ is $C_1$-$C_5$ alkyl or $C_1$-$C_5$ alkoxy are important intermediates for production of herbicides as described in U.S. Pat. No. 4,129,436. Particularly, p-methylphenethyl alcohol is, as described in European Patent Publication No. 003835, an intermediate in the production of N'-4-[2-(4-methylphenyl)ethoxy]phenyl-N-methoxy-N-methylurea, which exhibits a strong herbicidal activity against various weeds. Further, for instance, stearyl alcohol is, as well known, useful as the starting material for or the component in cosmetics.

Still, the carboxylic acids used as the starting material in the process of this invention are well known and commercially available. Also, they can be manufactured by conventional procedures. For instance, said arylacetic acids can be produced not only by reacting the corresponding aryl methyl halide with an alkaline metal cyanide and hydrolyzing the resultant arylacetonitrile (cf. Org.Syn.Coll.I., 107, 436 (1941)) but also by reacting the corresponding aryl methyl halide with carbon monoxide and an aqueous alcohol in the presence of a metal carbonyl and a basic agent (cf. Japanese Patent Publication (unexamined) No. 86339/1974).

While the carboxylic acids used as the starting material in the process of the invention may be produced by any method, the arylacetic acids as mentioned above are advantageously produced by the method as hereinafter explained. This method is to be understood as a part of the present invention.

Thus, the arylacetic acids of the formula:

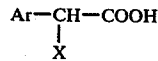

wherein Ar is as defined above and X is hydrogen can be produced in simple operations with good yields from the corresponding aryl aldehyde of the formula: Ar—CHO wherein Ar is as defined above by the reaction with carbon monoxide and water in the presence of a catalyst system comprising rhodium or its compound and hydrogen iodide.

As for production of arylacetic acids from aryl aldehydes, Japanese Patent Publication (unexamined) No. 136133/1977 discloses a process wherein the starting aryl aldehydes such as benzaldehyde are reacted with carbon monoxide and hydrogen in the presence of a catalyst system comprising rhodium oxide and iodine. In this process, however, high boiling by-products are produced in large amounts, and the yields of the desired arylacetic acids are low.

Japanese Patent Publication (unexamined) No. 56633/1978 discloses a process for production of arylacetic acids by reacting aryl aldehydes with carbon monoxide and water in the presence of a catalyst system comprising a Group VIII noble metal compound, bromine or iodine or their compound and a copper or silver compound. In order to achieve a satisfactory yield of the desired arylacetic acids, however, the use of an expensive copper or silver compound for the catalyst system is essential. Further, the separation and recovery of the catalyst components and the products from the reaction mixture are practically troublesome.

It has now been unexpectedly found that the use of a catalyst system comprising rhodium or its compound with hydrogen iodide, particularly in a certain specific ratio, can straightforwardly afford the corresponding arylacetic acids with high yields by the reaction of aryl aldehydes with carbon monoxide and water. The existence of any copper or silver compound in the catalyst system is not necessary.

According to this invention, an aryl aldehyde of the formula: Ar—CHO wherein Ar is as defined above is reacted with carbon monoxide and water in the presence of a catalyst system comprising rhodium or its compound and hydrogen iodide to give the corresponding arylacetic acid of the formula: Ar—$CH_2$—COOH wherein Ar is as defined above.

In the said formula for the starting aryl aldehyde, Ar is preferred to represent a substituted or unsubstituted monocyclic aromatic hydrocarbon group, particularly a phenyl group bearing optionally one to three substituents chosen from an alkyl having not more than 6 carbon atoms, an alkoxy having not more than 6 carbon atoms, an aryl having not more than 20 carbon atoms, an aralkyl having not more than 20 carbon atoms, an aryloxy having not more than 20 carbon atoms and a halogen. More preferably, Ar represents a phenyl group bearing optionally one or two substituents chosen from an alkyl having not more than 5 carbon atoms (especially methyl), an alkoxy having not more than 5 carbon atoms, fluorine and chlorine. Specific examples of the preferred aryl aldehyde are as follows: benzaldehyde, 2-methylbenzaldehyde, 4-methylbenzaldehyde, 2,4-dimethylbenzaldehyde, 4-isopropylbenzaldehyde, 4-t-butylbenzaldehyde, 4-methoxybenzaldehyde, 4-ethoxybenzaldehyde, 4-fluorobenzaldehyde, 4-chlorobenzaldehyde, etc. Among them, 4-methylbenzaldehyde is particularly favorable.

The catalyst system comprises rhodium or its compound and hydrogen iodide. As the rhodium compound, there may be used halides, oxides, oxo acids, oxo acid salts, carbonyl compounds, halogenocarbonyl compounds, nitrates, coordinated compounds having a ligand such as halogen, carbon monoxide, a nitrogen compound or a phosphorus compound, etc. of rhodium. Specific examples are rhodium trichloride, dirhodium trioxide, rhodium(II) acetate dimer, rhodium nitrate, tetrarhodium dodecacarbonyl, dirhodium octacarbonyl, trichlorotris(pyridine) rhodium(III), chlorocarbonylbis(triphenylphosphine) rhodium(I), chlorotris(triphenylphosphine) rhodium(I), hydridocarbonyltris(triphenylphosphine) rhodium(I), etc. Among them, rhodium halide compounds are preferable.

Rhodium or its compound may be as such used in the catalyst system. In alternative, the rhodium or its compounds may be supported on a porous carrier such as activated carbon, alumina, silica or celite. The amount of rhodium or its compound to be used is usually from $1 \times 10^{-5}$ to $1 \times 10^{-1}$ gram atom (in terms of rhodium), preferably from $1 \times 10^{-4}$ gram atom to $5 \times 10^{-2}$ gram atom, to 1 mole of the aryl aldehyde.

In addition to rhodium and its compound, the catalyst system requires hydrogen iodide as an essential component. The amount of hydrogen iodide may be usually from 1 to 10 moles to one gram atom of rhodium or one mole of its compound. When the amount of hydrogen iodide is out of the said range, the lowering of the reaction rate, the increase of the by-products, the decrease of the arylacetic acid, etc. are observed. Hydrogen iodide may be incorporated into the catalyst system in the form of aqueous solution.

Either the catalyst system as previously prepared may be introduced into the reaction system or the components of the catalyst system may be added directly to the reaction system.

The amount of water as the reactant may be from 1 to 50 moles, preferably from 1 to 10 moles, to one mole of the aryl aldehyde. The use of any solvent is not necessarily required, but usually an inert solvent such as hexane, cyclohexane, benzene, toluene or xylene is employed.

The reaction is normally carried out at a temperature of 50° to 250° C., preferably of 100° to 200° C., under a carbon monoxide partial pressure of 10 to 300 atm, favorably of 20 to 150 atm. The carbon monoxide may be used as such or in a mixture with any inert gas. The reaction time depends on the reaction temperature and is usually from 0.1 to 10 hours. The reaction may be carried out batchwise or continuously. For preventing the reaction system from contamination with a metal compound dissolving out of the wall of the reaction vessel, its inner surface is favorably provided with corrosion-resistance. Thus, the use of such reactor as glass-lined or made of Hastelloy C or titanium is favorable, although a stainless steel (e.g. SUS 316) made one is not preferred.

As the result of the above reaction, there is produced an arylacetic acid corresponding to the starting aryl aldehyde in a good yield. Separation of the produced arylacetic acid from the reaction mixture may be accomplished by a per se conventional procedure such as distillation, extraction or crystallization.

Practical and presently preferred embodiments of the invention are illustratively shown in the following Examples wherein the identification and quantitative analysis of the products were carried out by means of IR, NMR and gas chromatography. Further, the conversion, yield and selectivity were calculated according to the following equations:

$$\text{Conversion (\%)} = \frac{\text{Mole number of reacted starting material}}{\text{Mole number of used starting material}} \times 100$$

$$\text{Yield (\%)} = \frac{\text{Mole number of product}}{\text{Mole number of used starting material}} \times 100$$

$$\text{Selectivity (\%)} = \frac{\text{Mole number of product}}{\text{Mole number of reacted starting material}} \times 100$$

EXAMPLE 1

Into a 50 ml volume stainless steel made autoclave equipped with a magnetic stirrer and inserted with a glass tube, p-methylphenylacetic acid (0.6 g), dehydrated dioxane (10 ml), dirhenium heptoxide (60 mg) and triethylamine (4.3 mg) were charged, and the inner atmosphere was replaced by nitrogen gas. Hydrogen gas was pressurized therein up to 100 atm. The reaction was carried out at 162° C. for 5 hours while stirring. After cooling to room temperature, the reaction mixture was subjected to gas chromatographic analysis to give the following results: conversion of p-methylphenylacetic acid, 98.5%; yield of p-methylphenethyl alcohol, 92.4%; selectivity to p-methylphenethyl alcohol, 93.8%; yield of ethyltoluene, 0.5%.

COMPARATIVE EXAMPLE 1

In the same manner as in Example 1 but not using triethylamine, the reaction was carried out to give the following results: conversion of p-methylphenylacetic acid, 99.2%; yield of p-methylphenethyl alcohol, 74.3%; selectivity to p-methylphenethyl alcohol, 74.9%; yield of ethyltoluene, 10.2%.

EXAMPLES 2 TO 5 AND COMPARATIVE EXAMPLES 2 TO 5

In the same manner as in Example 1 or Comparative Example 1 but using an arylacetic acid as the starting material, the reaction was carried out to give the results as shown in Table 1.

TABLE 1

| Example | Arylacetic acid | Conversion of arylacetic acid (%) | Yield of 2-arylethanol (%) | Selectivity to 2-arylethanol (%) |
|---|---|---|---|---|
| 2 | Phenylacetic acid | 97.8 | 87.7 | 89.7 |
| 3 | p-Chlorophenylacetic acid | 96.5 | 80.1 | 83.0 |
| 4 | 1-Naphthylacetic acid | 44.3 | 40.1 | 90.5 |
| 5 | o-Methylphenylacetic acid | 96.3 | 88.1 | 91.5 |
| Comparative 2 | Phenylacetic acid | 94.2 | 74.6 | 79.2 |
| Comparative 3 | p-Chlorophenylacetic acid | 89.0 | 62.4 | 70.6 |
| Comparative 4 | 1-Naphthyl-(*1) acetic acid | 59.0 | 49.0 | 83.1 |
| Comparative 5 | o-Methylphenylacetic acid | 95.2 | 73.8 | 77.5 |

Note:
(*1) Reaction was effected for 9 hours.

EXAMPLES 6 TO 10

In the same manner as in Example 1 but using any other organic base in place of triethylamine, the reaction was carried out to give the results as shown in Table 2.

TABLE 2

| | Organic base | | Conversion of p-methylphenylacetic acid (%) | Selectivity to p-methylphenethyl alcohol (%) |
|---|---|---|---|---|
| Example | Kind | Amount (mg) | | |
| 6 | Pyridine | 5.9 | 65.9 | 88.5 |
| 7 | Morpholine | 6.0 | 75.4 | 88.9 |
| 8 | Isoquinoline | 6.4 | 47.4 | 86.9 |
| 9 | Triphenylphosphine | 5.0 | 70.9 | 99.6 |
| 10 | Tri-n-butylphosphine | 6.6 | 75.2 | 99.8 |

EXAMPLE 11

In the same manner as in Example 1 but using 4-methylphenylacetic acid (1 g), triethylamine (7.3 mg) and toluene (5 ml) in place of dioxane (10 ml), the reaction was carried out to give the following results: conversion of 4-methylphenylacetic acid, 98.1%; yield of p-methylphenethyl alcohol, 85.2%; selectivity to p-methylphenethyl alcohol, 86.8%; yield of ethyltoluene, 2.3%; yield of (p-methylphenyl)2-ethyl p-methylphenylacetate, 4.7%.

COMPARATIVE EXAMPLE 6

In the same manner as in Example 11 but not using triethylamine, the reaction was carried out to give the following results: conversion of p-methylphenylacetic acid, 98.3%; yield of p-methylphenethyl alcohol, 73.7%; selectivity to p-methylphenethyl alcohol, 75.0%; yield of ethyltoluene, 3.2%; yield of (p-methylphenyl)-2-ethyl p-methylphenylacetate, 8.2%.

EXAMPLES 12 TO 18

Into a 50 ml volume stainless steel made autoclave equipped with a magnetic stirrer and inserted with a glass tube, a carboxylic acid (1.0 g), dehydrated dioxane (5 ml or 10 ml), dirhenium heptoxide (100 mg) and triethylamine (4.3 mg) were charged, and the inner atmosphere was replaced by nitrogen. Hydrogen gas was pressurized therein up to 100 atm. The reaction was carried out at a designed temperature for a designed period of time while stirring. After cooling, the reaction mixture was subjected to gas chromatographic analysis to give the results as shown in Table 3.

COMPARATIVE EXAMPLES 7 TO 13

In the same manner as in Examples 12 to 18 but not using triethylamine, the reaction was carried out to give the results as shown in Table 4.

carried out at 150° C. for 4 hours while stirring. After cooling, the reaction mixture was subjected to gas chromatographic analysis to give the following results: conversion of p-methylbenzaldehyde, 99.6%; yield of p-methylphenylacetic acid, 94.5%; selectivity to p-methylphenylacetic acid, 94.9%; yield of p-xylene, 3.5%.

EXAMPLE 20

In the same manner as in Example 19 but using benzaldehyde (1.06 g), the reaction was carried out. The reaction mixture was subjected to gas chromatographic analysis to give the following results: conversion of benzaldehyde, 94.3%; yield of phenylacetic acid, 87.9%; selectivity to phenylacetic acid, 93.2%; yield of toluene, 6.0%.

EXAMPLES 21 AND 22

In the same manner as in Example 19 but adjusting the pressure of carbon monoxide to a pressure of 100

TABLE 3

| Example | Carboxylic acid | Solvent (ml) | Reaction temperature (°C.) | Reaction time (hr) | Conversion of carboxylic acid (%) | Yield of alcohol (%) | Selectivity to alcohol (%) |
|---|---|---|---|---|---|---|---|
| 12 | Caproic acid | 5(*1) | 210 | 2 | 100 | 96.1 | 96.1 |
| 13 | Stearic acid | 5 | 180 | 2 | 97.0 | 90.8 | 93.6 |
| 14 | ε-Oxycaproic acid | 4(*2) | 210 | 5 | 98.3 | 88.4 | 89.9 |
| 15 | Monochloroacetic acid | — | 205 | 7 | 96.0 | 87.0 | 90.6 |
| 16 | Benzoic acid | 5 | 160 | 5 | 90.0 | 76.9 | 85.4 |
| 17 | p-Toluic acid | 10 | 160 | 6 | 89.2 | 71.9 | 80.9 |
| 18 | m-Phenoxybenzoic acid | 10 | 160 | 7 | 92.9 | 74.3 | 80.0 |

Note:
(*1)dioxane (2.5 ml) + water (2.5 ml);
(*2)water

TABLE 4

| Comparative Example | Carboxylic acid | Solvent (ml) | Reaction temperature (°C.) | Reaction time (hr) | Conversion of carboxylic acid (%) | Yield of alcohol (%) | Selectivity to alcohol (%) |
|---|---|---|---|---|---|---|---|
| 7 | Caproic acid | 5(*1) | 210 | 5 | 97.8 | 81.8 | 83.6 |
| 8 | Stearic acid | 5 | 180 | 2 | 82.5 | 69.1 | 83.8 |
| 9 | ε-Oxycaproic acid | 4(*2) | 210 | 5 | 90.0 | 71.9 | 79.9 |
| 10 | Monochloroacetic acid | — | 205 | 7 | 84.8 | 62.4 | 73.6 |
| 11 | Benzoic acid | 5 | 160 | 5 | 71.9 | 41.6 | 57.9 |
| 12 | p-Toluic acid | 10 | 160 | 6 | 73.8 | 40.1 | 54.3 |
| 13 | m-Phenoxybenzoic acid | 10 | 160 | 7 | 88.8 | 51.8 | 58.3 |

Note:
(*1)dioxane (2.5 ml) + water (2.5 ml);
(*2)water

EXAMPLE 19

Into a 50 ml volume stainless steel made autoclave equipped with a magnetic stirrer and inserted with a glass tube, p-methylbenzaldehyde (1.20 g), water (0.54 g), rhodium trichloride (0.2 mmol), 57% hydrogen iodide solution (0.13 g) and benzene (5 ml) were charged, and the inner atmosphere was replaced by nitrogen gas. Carbon monoxide was pressurized therein up to 50 atm. The molar ratio of HI/RhCl$_3$ was 3.1. The reaction was atm and varying the amount of hydrogen iodide, the reaction was carried out. The results are shown in Table 5.

COMPARATIVE EXAMPLES 14 TO 17

In the same manner as in Example 21 but using iodine or iodine and cuprous iodide in place of hydrogen iodide and varying the reaction time, the reaction was carried out. The results are shown in Table 5.

TABLE 5

| Example | RhCl₃ (mmol) | HI (mmol) | I₂ (mmol) | CuI (mmol) | Reaction temperature (°C.) | Reaction time (hr) | Conversion (%) | Yield of p-methyl-phenylacetic acid (%) | Yield of p-xylene (%) |
|---|---|---|---|---|---|---|---|---|---|
| 21 | 0.2 | 1.0 | 0 | 0 | 150 | 4 | 97.9 | 91.3 | 5.5 |
| 22 | 0.2 | 0.6 | 0 | 0 | 150 | 4 | 98.2 | 90.2 | 4.3 |
| Comparative 14 | 0.2 | 3.76 | 0 | 0 | 150 | 4 | 100 | 52.3 | 42.0 |
| Comparative 15 | 0.2 | 0 | 1.0 | 0 | 150 | 2 | 71.4 | 60.4 | 5.9 |
| Comparative 16 | 0.2 | 0 | 0.5 | 0 | 150 | 4 | 91.0 | 65.7 | 6.6 |
| Comparative 17 | 0.2 | 0 | 1.0 | 0.6 | 150 | 2 | 100 | 70.9 | 20.6 |

EXAMPLE 23

In the same manner as in Example 19 but using a 50 ml volume Hastelloy C made autoclave equipped with a magnetic stirrer and not inserted with a glass tube, the reaction was carried out. The analysis of the reaction mixture revealed the following results: conversion of p-methylbenzaldehyde, 100%; yield a p-methyl-phenylac.tic acid, 90.7%; yield of p-xylene, 3.0%.

EXAMPLE 24

Into a 50 ml volume stainless steel made autoclave equipped with a magnetic stirrer and inserted with a glass tube, adipic acid (1.0 g), a mixture of dioxane and water (1:1) (5 ml), dirhenium heptoxide (100 mg) and triethylamine (7.2 mg) were charged, and the inner atmosphere was replaced by nitrogen gas. Hydrogen gas was pressurized therein up to 100 atm. The reaction was carried out at 210° C. for 4 hours while stirring. After cooling to room temperature, the reaction mixture was subjected to gas chromatographic analysis to give the following results: conversion of adipic acid, 95.3%; yield of 1,6-hexamethylenediol, 55.9%; yield of ε-oxycaproic acid, 23.0%.

COMPARATIVE EXAMPLE 18

In the same manner as in Example 24 but not using triethylamine, the reaction was carried out. The reaction mixture was subjected to gas chromatographic analysis to give the following results: conversion of adipic acid, 84.6%; yield of 1,6-hexamethylenediol, 17.7%; yield of ε-oxycaproic acid, 33.0%.

What is claimed is:

1. A process for preparing an alcohol from the corresponding carboxylic acid by reducing said carboxylic acid with hydrogen in the presence of a rhenium catalyst, characterized in that at least one organic base selected from the group consisting of organic amines and organic phosphines is present in the reaction system.

2. The process according to claim 1, wherein the rhenium catalyst is a rhenium oxide.

3. The process according to claim 1, wherein the organic base is selected from the group consisting of tertiary amines and tri-substituted phosphines.

4. The process according to claim 1, wherein the amount of the organic base is from $10^{-4}$ to 10 moles to one mole of the rhenium catalyst.

5. The process according to claim 1, wherein the carboxylic acid has at least one carboxyl group and does not include any atom or group which prevents or interferes the relevant reduction.

6. The process according to claim 5, wherein the carboxylic acid is the one of the formula: R—COOH wherein R is a substituted or unsubstituted, aliphatic, aromatic or araliphatic group.

7. The process according to claim 6, wherein the carboxylic acid is the one of the formula:

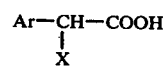

wherein Ar is a substituted or unsubstituted, monocyclic or condensed polycyclic, aromatic hydrocarbon group and X is hydrogen or alkyl having not more than 6 carbon atoms.

8. The process according to claim 7, wherein Ar is a phenyl group bearing optionally one to three substituents chosen from alkyl having not more than 6 carbon atoms, alkoxy having not more than 6 carbon atoms, aryl having not more than 20 carbon atoms, aralkyl having not more than 20 carbon atoms, aryloxy having not more than 20 carbon atoms and halogen.

9. The process according to claim 8, wherein X is hydrogen.

10. The process according to claim 9, wherein the carboxylic acid is the one prepared by reacting the corresponding aldehyde with carbon monoxide and water in the presence of a catalyst system comprising rhodium or its compound with hydrogen iodide.

11. A process for preparing a carboxylic acid of of the formula: Ar—CH₂—COOH wherein Ar is a substituted or unsubstituted, monocyclic or condensed polycyclic, aromatic hydrocarbon group by reacting the corresponding aldehyde of the formula: Ar—CHO wherein Ar is as defined above with carbon monoxide and water in the presence of a catalyst system, characterized in that the catalyst system comprises rhodium or its compound with hydrogen iodide, the molar ratio (gram atom ratio) of hydrogen iodide to rhodium or its compound being from 1 to 10.

12. The process according to claim 11, wherein Ar is a phenyl group bearing optionally one to three substituents chosen from alkyl having not more than 6 carbon atoms, alkoxy having not more than 6 carbon atoms, aryl having not more than 20 carbon atoms, aralkyl having not more than 20 carbon atoms, aryloxy having not more than 20 carbon atoms and halogen.

* * * * *